United States Patent
Melkonyan et al.

(10) Patent No.: US 8,383,335 B2
(45) Date of Patent: Feb. 26, 2013

(54) METHOD FOR DIAGNOSIS AND MONITORING OF VIRAL INFECTION BY ANALYSIS OF VIRAL TRANSRENAL NUCLEIC ACIDS IN URINE

(75) Inventors: Hovsep Melkonyan, Princeton, NJ (US); Angela Cannas, Arbus (IT); Louis David Tomei, Genazzano (IT); Samuil R. Umansky, Princeton, NJ (US)

(73) Assignee: Trovagene, Inc., San Diego, CA (US)

( * ) Notice: Subject to any disclaimer, the term of this patent is extended or adjusted under 35 U.S.C. 154(b) by 0 days.

(21) Appl. No.: 13/114,289

(22) Filed: May 24, 2011

(65) Prior Publication Data
US 2012/0021404 A1 Jan. 26, 2012

Related U.S. Application Data

(63) Continuation of application No. 11/137,935, filed on May 25, 2005, now Pat. No. 7,973,154.

(30) Foreign Application Priority Data

Feb. 17, 2005 (IT) .............................. RM2005A0067

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........... 435/5; 435/6.1; 435/6.11; 435/6.12; 435/91.2; 536/24.32; 536/24.33

(58) Field of Classification Search ........................ None
See application file for complete search history.

(56) References Cited

U.S. PATENT DOCUMENTS

| | | |
|---|---|---|
| 5,168,039 A | 12/1992 | Crawford et al. |
| 5,631,130 A | 5/1997 | Leckie et al. |
| 5,712,385 A | 1/1998 | McDonough et al. |
| 6,251,638 B1 | 6/2001 | Umansky et al. |
| 6,287,820 B1 | 9/2001 | Umansky et al. |
| 6,368,800 B1 | 4/2002 | Smith et al. |
| 6,492,144 B1 | 12/2002 | Umansky et al. |
| 2002/0119478 A1 | 8/2002 | Umansky et al. |
| 2003/0152591 A1 | 8/2003 | Sablon et al. |
| 2003/0152982 A1 | 8/2003 | De Beenhouwer et al. |
| 2004/0053264 A1 | 3/2004 | Park |
| 2006/0183107 A1 | 8/2006 | Melkonyan et al. |
| 2007/0037181 A1 | 2/2007 | Melkonyan et al. |
| 2010/0068711 A1 | 3/2010 | Umansky et al. |

FOREIGN PATENT DOCUMENTS

| | | |
|---|---|---|
| WO | WO-9504140 A1 | 2/1995 |
| WO | WO-9854364 A1 | 12/1998 |
| WO | WO-9858086 A2 | 12/1998 |
| WO | WO-2006088895 A2 | 8/2006 |
| WO | WO-2006089203 A2 | 8/2006 |

OTHER PUBLICATIONS

Tomei et al Clinical Chemistry. Annual Meeting of the American Association for Clinical Chemistry. Jul. 24-28, 2005,vol. 51 (Suppl 6): p. A180.*
Aceti et al. "Identification of HIV Patients with Active Pulmonary Tuberculosis Using Urine Based Polymerase Chain Reaction Assay." *Thorax*. 54(1999):145-146.
Achtman et al. "Recombination and Clonal Groupings within *Helicobacter pylori* from Different Geographical Regions." *Molec. Microbiol*. 32.3(1999):459-470.
Ahern. "Biochemical, Reagent Kits Offver Scientists Good Return on Investment." *The Scientist*. 9.15(1995):20-24.
Akopyanz et al. "DNA Diversity Among Clinical Isolates of *Helicobacter pylori* Detected by PCR-Based RAPD Fingerprinting." *Nucl. Acids Res*. 20.19(1992):5137-5142.
Alm et al. "Genomic-Sequence Comparison of Two Unrelated Isolates of the Human Gastric Pathogen *Helicobacter pylori*." *Nature*. 397(1999):176-180.
Al-Yatama et al. "Detection of Y-Chromosome-Specific DNA in the Plasma and Urine of Pregnant Women Using Nested Polymerase Chain Reaction." *Prenat. Diagn*. 21(2001):399-402.
Atherton et al. "Vacuolating Cytotoxin (*vacA*) Alleles of *Helicobacter pylori* Comprise Two Geographically Widespread Types, m1 and m2, and Have Evolved Through Limited Recombination." *Curr. Microbiol*. 39.4(1999):211-218.
Atherton. "The Clinical Relevance of Strain Types of *Helicobacter pylori*." *Gut*. 40.6(1997):701-703.
Axon. "Are All Helicobacters Equal?" *Gut*. 45.S1(1999):1-14.
Barany. "Genetic Disease Detection and DNA Amplification Using Cloned Thermostable Ligase." *PNAS*. 88.1(1991):189-193.
Bekkaoui et al. "Cycling Probe Technology with Rnase H Attached to an Oligonucleotide." *BioTech*. 20.2(1996):240-248.
Belli et al. "Simplified Polymerase Chain Reaction Detection of New World Leishmania in Clinical Specimens of Cutaneous Leishmaniasis." *Am. J. Trop. Med. Hyg*. 58.1(1998):102-109.
Bickley et al. "Evaluation of the Polymerase Chain Reaction for Detecting the Urease C Gene of *Helicobacter pylori* in Gastric Biopsy Samples and Dental Plaque." *J. Med. Microbiol*. 39(1993):338-344.
Blackwood et al. "Reassessment of Sequence-Based Targets for Identification of *Bacillus* Species." *J. Clin. Microbiol*. 42(2004):1626-1630.
Blaser et al. "Infection with *Helicobacter pylori*Strains Possessing *cagA* is Associated with an Increased Risk of Developing Adenocarcinoma of the Stomach." *Cancer Res*. 55(1995):2111-2115.
Botezatu et al. "Genetic Analysis of DNA Excreted in Urine: A New Approach for Detecting Specific Genomic DNA Sequences from Cells Dying in an Organism." *Clin. Chem*. 8.46(2000):1078-1084.
Buffone et al. "Improved Amplification of Cytomegalovirus DNA from Urine After Purification of DNA with Glass Beads." *Clin. Chem*. 37(1991):1945-1949.

(Continued)

*Primary Examiner* — Carla Myers
(74) *Attorney, Agent, or Firm* — Patentique PLLC (57) ABSTRACT

The present invention relates to methods for diagnosis or monitoring of viral infection by detecting the presence of transrenal viral nucleic acids or nucleic acids of viral origin in urine sample, with or without isolation of nucleic acids from a urine sample. The analysis of the nucleic acids is performed through hybridization of the nucleic acids with specific probes, or through a chain amplification reaction with specific primers. The methods are applicable to all viral pathogenic agents, including RNA, DNA, episomal, or integrated viruses.

18 Claims, 3 Drawing Sheets

OTHER PUBLICATIONS

Chan et al. "Molecular Characterization of Circulating EBV DNA in the Plasma of Nasopharyngeal Carcinoma and Lymphoma Patients." *Cancer Res.* 63(2002):2028-2032.

Clayton et al. "Sensitive Detection of *Helicobacter pylori* by Using Polymerase Chain Reaction." *J. Clin. Microbiol.* 30(1992):192-200.

Cover et al. "Divergence of Genetic Sequences for the Vacuolating Cytotoxin Among *Helicobacter pylori* Strains." *J. Biol. Chem.* 269(1994):10566-10573.

Del Portillo et al. "Amplification of a Species-Specific DNA Fragment of *Mycobacterium tuberculosis* and its Possible Use in Diagnosis." *J. Clin. Microbiol.* 29(1991):2163-2168.

Disch et al. "Detection of Circulating *Leishmania chagasi* DNA for the Non-Invasive Diagnosis of Human Infection." *Trans. Royal Soc. Trop. Med. Hyg.* 97.4(2003):391-395.

Disch et al. "Rapid Clearance of Circulating *Leishmania* Kinetoplast DNA After Treatment of Visceral Leishmaniasis." *Acta Trop.* 92.3(2004):279-283.

Drago et al. "Real-Time PCR Assay for Rapid Detection of *Bacillus anthracis* Spores in Clinical Samples." *J. Clin. Microbiol.* 40(2002):4399.

Drobniewski et al. "Modern Laboratory Diagnosis of Tuberculosis." *Lancet Inf. Dis.* 3.3(2003):141-147.

Echavarria et al. "PCR Method for Detection of Adenovirus in Urine of Healthy and Human Immunodeficiency Virus-Infected Individuals." *J. Clin. Microbiol.* 36.11(1998):3323-3326.

Elzinga et al. "Scale Up: Meeting Targets in Global Tuberculosis Control." *Lancet.* 363.9411(2004):814-819.

Fasanella et al. "Detection of Anthrax Vaccine Virulence Factors by Polymerase Chain Reaction." *Vacc.* 19.30(2001):4214-4218.

Fenves. "Legionnaires' Disease Associated with Acute Renal Failure: A Report of Two Cases and Review of the Literature." *Clin. Nephrol.* 23.2(1985):96-100.

Frazier et al. "DNA Probes for Detecting *Coxiella burnetii* Strains." *Acta Virol.* 36.1(1992):83-89.

Friedlander. "DNA Release as a Direct Measure of Microbiol Killing by Phagocytes." *Infect. Immun.* 22(1978):148-154.

Gal et al. "Detection of *Plasmodium falciparum* DNA in Plasma." *Ann. NY Acad. Sci.* 945.1(2001):234-238.

Galvão de Araujo et al. "A Retrospective Survery of Dengue Virus Infection in Fatal Cases from an Epidemic in Brazil." *J. Virol. Methods.* 155.1(2009):34-38.

Goman et al. "The Complete Sequence of a *Plasmodium malariae* SSUrRNA Gene and its Comparison to Other Plasmodial SSUrRNA Genes." *Mol. Biochem. Parasitol.* 45(1991):281-288.

Green et al. "Demonstration of a Capsule Plasmid in *Bacillus anthracis.*" *Infect. Immun.* 49(1985):291-297.

Haines et al. "Interstitial Nephritis in a Patient with Legionnaires' Disease." *Postgrad. Med.* 81.3(1987):77-79.

Hammar et al. "Rapid Detection of *Helicobacter pylori* in Gastric Biopsy Material by Polymerase Chain Reaction." *J. Clin. Microbiol.* 30(1992):54-58.

Hemal et al. "Polymerase Chain Reaction in Clinically Suspected Genitourinary Tuberculosis: Comparison with Intravenous Urography, Bladder Biopsy and Urine Acid Fast *Bacilli* Culture." *Urol.* 56.4(2000):570-574.

Higgins et al. "A Field Investigation of *Bacillus anthracis* Contamination of U.S. Department of Agriculture and Other Washington, D.C., Buildings During the Anthrax Attack of Oct. 2001." *Appl. Environ. Microbiol.* 69(2003):593-599.

Ho et al. "Direct Molecular Detection of Nucleic Acids by Fluorescence Signal Amplifcation." *J. Am. Chem. Soc.* 127.36:12673-12676, 2005.

Ho et al. "Direct Polymerase Chain Reaction Test for Detection of *Helicobacter pylori* in Humans and Animals." *J. Clin. Microbiol.* 29(1991):2543-2549.

Hurtle et al. "Detection of the *Bacillus anthracis gyrA* Gene by Using a Minor Groove Binder Probe." *J. Clin. Microbiol.* 42(2004):179-185.

Jeong et al. "Genotyping of the JC Virus in Urine Samples of Healthy Korean Individuals." *J. Med. Virol.* 72.2(2004):281-289.

Kafwabulula et al. "Evaluation of PCR-Based Methods for the Diagnosis of Tuberculosis by Identification of Mycobacterial DNA in Urine Samples." *Int. J. Tuberc. Lung Dis.* 6.8(2002):732-737.

Keim et al. "Multiple-Locus Variable-Number Tandem Repeat Analysis Reveals Genetic Relationships within *Bacillus anthracis.*" *J. Bacteriol.* 182(2000):2928-2936.

Kleanthous et al. "Characterization of a Plasmid from *Helicobacter pylori* Encoding a Replication Protein Common to Plasmids in Gram-Positive Bacteria." *Molec. Microbiol.* 5.10(1991):2377-2389.

Koide et al. "Fragmentation of Cell-Free Fetal DNA in Plasma and Urine of Pregnant Women." *Prenat. Diagn.* 25.7(2005):604-607.

Kolk et al. "Detection of *Mycobacterium tuberculosis* in Clinical Samples by Using Polymerase Chain Reaction and a Nonradioactive Detection System." *J. Clin. Microbiol.* 30(1992):2567-2575.

Kox et al. "Early Diagnosis of Tuberculosis Meningitis by Polymerase Chain Reaction." *Neurol.* 45(1995):2228-2232.

Lee et al. "Programmed Cell Death in the Unicellular Protozoan Parasite *Leishmania.*" *Cell Death Differentiation.* 9(2002):53-64.

Leppia. "Anthrax Toxins." *Handbook Nat. Toxins.* 8(1995):543-572.

Li et al. "HIV-1 DNA Proviral Sequences in Fresh Urine Pellets from HIV-1 Seropositive Persons." *Lancet.* 335.8705(1990):1590-1591.

Lichtenstein et al. "Circulating Nucleic Acids and Apoptosis." *Ann. NY Acad. Sci.* 945(2001):239-249.

Lo et al. "Molecular Testing of Urine: Catching DNA on the Way Out." *Clin. Chem.* 46.8(2000):1039-1040.

Logan et al. "*Bacillus* and Other Aerobic Endospore-Forming Bacteria." *Manual of Clinical Microbiology.* 8(2004):445-460.

Lu et al. "Comparison of Five PCR Methods for Detection of *Helicobacter pylori* DNA in Gastric Tissues." *J. Clin. Microbiol.* 37(1999):772-774.

Maiwald et al. "Detection of *Legionella* DNA in Human and Guinea Pig Urine Samples by the Polymerase Chain Reaction." *Eur. J. Clin. Microbiol. Infect. Dis.* 14.1(1995):25-33.

Maiwald et al. "Evaluation of the Detection of *Borrelia burgdorferi* DNA in Urine Samples by Polymerase Chain Reaction." *Infect.* 23.3(1995):173-179.

Marei et al. "Evaluation of a Rapid Bacteriophage-Based Method for the Detection of *Mycobacterium tuberculosis* in Clinical Samples." *J. Med. Microbiol.* 52(2003):331-335.

Marmur et al. "Strand Separation and Specific Recombination in Deoxyribonucleic Acids: Biological Studies." *Biochem.* 46(1960):453-461.

McCutchan et al. "Primary Sequences of Two Small Subunit Ribosomal RNA Genes From *Plasmodium falciparum.*" *Molec. Biochem. Parasitol.* 28(1988):63-68.

Mercier et al. "Detection of *Borrelia burgdorferi* DNA by Polymerase Chain Reaction in Urine Specimens of Patients with Erythema Migrans Lesion." *Molec. Cell. Probes.* 11(1997):89-94.

Mikesell et al. "Plasmids, Pasteur, and Anthrax." *ASM News.* 49(2002):320-322.

Mobley. "Defining *Helicobacter pylori* as a Pathogen: Strain Heterogeneity and Virulence." *Am. J. Med.* 100.S5A(1996):5A-2S.

Moussa et al. "Rapid Diagnosis of Genitourinary Tuberculosis by Polymerase Chain Reaction and Non-Radioactive DNA Hybridization." *J. Urol.* 164(2000):584-588.

Mukopadhyay et al. "A Structural Perspective on the Flavirus Life Cycle." *Nat. Rev. Microbiol.* 3.1(2005):13-22.

Murdoch et al. "Use of the Polymerase Chain Reaction to Detect *Legionella* DNA in Urine and Serum Samples from Patients with Pneumonia." *Clin. Infect. Dis.* 23(1996):475-480.

Navarre et al. "Pathogen-Induced Apoptosis of Macrophages: A Common End for Different Pathogenic Strategies." *Cell. Microbiol.* 2.4(2000):265-273.

Oggioni et al. "Protocol for Real-Time PCR Identification of Anthrax Spores From Nasal Swabs after Broth Enrichment." *J. Clin. Microbiol.* 40.11(2002):3956-3963.

Piersimoni et al. "Performance Assessment of Two Commercial Amplification Assays for Direct Detection of *Mycobacterium tuberculosis* Complex From Respiratory and Extrapulmonary Specimens." *J. Clin. Microbiol.* 40.11(2002):4138-4142.

Piersimoni et al. "Relevance of Commercial Amplification Methods for Direct Detection of *Mycobacterium tuberculosis* Complex in Clinical Samples." J. Clin. Microbiol. 41.12(2003):5355-5365.

Poloni et al. "Detection of Dengue Virus in Saliva and Urine by Real Time RT-PCR." *Virol. J.* 7(2010):22.

Pornthanaskasem et al. "Human Papillomavirus DNA in Plasma of Patients With Cervical Cancer." *BMC Cancer*. 1(2001):2.

Poulter et al. "Acute Interstitial Nephritis Complicating Legionaires' Disease." *Clin. Nephrol*. 15.4(1981):216-220.

Qari et al. "Phylogenetic Relationship Among the Malaria Parasites Based on Small Subunit rRNA Gene Sequences: Monophyletic Nature of the Human Malaria Parasite, *Plasmodium falciparum*." *Molec. Phylogen. Evol*. 6.1(1996):157-165.

Qi et al. "Biological Characteristics of Dengue Virus and Potential Targets for Drug Design." *Acta Biochim. Biophys. Sin*. 40.2(2008):91-101.

Qi et al. "Utilization of the *rpoB* Gene as a Specific Chromosomal Marker for Real-Time PCR Detection of *Bacillus anthracis*." *App. Environ. Microbiol*. 67.8(2001):3720-3727.

Sarmiento et al. "Assessment by Meta-Analysis of PCR for Diagnosis of Smear-Negative Pulmonary Tuberculosis." *J. Clin. Microbiol*. 41.7(2003):3233-3240.

Schürmann et al. "Pulmonary and Extrapulmonary Manifestations of *L. pneumophila*." *Zbl. Bakt. Hyg., I. Abt. Orig. A*. 255(1983):120-126.

Seah et al. "Semi-Nested PCR Using NS3 Primers for the Detection and Typing of Dengue Viruses in Clinical Serum Specimens." *Clin. Diagn. Virol*. 4.2(1995):113-120.

Shilo et al. "DNA Sequences Homologous to Vertebrate Oncogenes are Conserved in *Drosphila melanogaster*." *PNAS*. 78.11(1981):6789-6792.

Su et al. "Human Urine Contains Small, 150 to 250 Nucleotide-Sized, Soluble DNA Derived from the Circulation and May Be Useful in the Detection of Colorectal Cancer." *J. Mol. Diag*. 6.2(2004):101-107.

Su et al. "Transrenal DNA as a Diagnostic Tool—Important Technical Notes." *Ann. NY Acad. Sci*. (2004):81-89.

Tamarit et al. "Human Cytomegalovirus (HCMV)-Specific CD4+ T Lymphocyte Response in AIDS Patients With No Past or Current HCMV Disease Following HAART." *J. Clin. Virol*. 29.4(2004):308-314.

Tomb et al. "The Complete Genome Sequence of the Gastric Pathogen *Helicobacter pylori*." *Nature*. 388(1997):539-547.

Torrea et al. "PCR-Based Detection of the *Mycobacterium tuberculosis* Complex in Urine of HIV-Infected and Uninfected Pulmonary and Extrapulmonary Tuberculosis Patients in Burkina Faso." *J. Med. Microbiol*. 54(2005):39-44.

Tummuru et al. "Cloning and Expression of a High-Molecular-Mass Major Antigen of *Helicobacter pylori*: Evidence of Linkage to Cytotoxin Production." *Infect. Immun*. 61.5(1993):1799-1809.

Uchida et al. "Virulence and Immunogenicity in Experimental Animals of *Bacillus anthracis* Strains Harbouring of Lacking 110 Mda and 60 Mda Plasmids." *J. Gen. Microbiol*. 132(1986):557-559.

Umansky et al. "In vivo DNA Degradation in Thymocytes of Gamma-Irradiated or Hydrocortisone-Treated Rats." *Biochim. Biophys. Acta*. 655(1982):9-17.

Utting et al. "Microsatellite Analysis of Free Tumor DNA in Urine, Serum, and Plasma of Patients: A Minimally Invasive Method for the Detection of Bladder Cancer." *Clin. Cancer Res*. 8(2002):35-40.

Valentine et al. "Detection of *Helicobacter pylori* by Using the Polymerase Chain Reaction." *J. Clin. Microbiol*. 29.4(1991):689-695.

van Vollenhoven et al. "Polymerase Chain Reaction in the Diagnosis of Urinary Tract Tuberculosis." *Urol. Res*. 24(1996):107-111.

Walker et al. "Multiplex Strand Displacement Amplification (SDA) and Detection of DNA Sequences from *Mycobacterium tuberculosis* and Other Mycobacteria." *Nucl. Acids Res*. 22.13(1994):2670-2677.

Wang et al. "Preferential Isolation of Fragmented DNA Enhances the Detection of Circulating Mutated k-*ras* DNA." *Clin. Chem*. 50.1(2004):211-213.

Waters et al. "Partial Sequence of the Asexually Expressed SU rRNA Gene of *Plasmodium vivax*." *Nucl. Acids Res*. 17.5(1989):2135.

Wegmüller et al. "Rapidly Progressive Glomerulonephritis Accompanying Legionnaires' Disease." *Arch. Intern. Med*. 145(1985):1711-1713.

Welkos. "Plasmid-Associated Virulence Factors of Non-Toxigenic (pX01) *Bacillus anthracis*." *Microbiol. Pathogen*. 10(1991):183-198.

Zambardi et al. "Rapid Diagnosis of *Mycobacterium tuberculosis* Infections by an ELISA-Like Detection of Polymerase Chain Reaction Products." *Molec. Cell. Probes*. 9(1995):91-99.

\* cited by examiner

METHOD FOR DIAGNOSIS AND MONITORING OF VIRAL INFECTION BY ANALYSIS OF VIRAL TRANSRENAL NUCLEIC ACIDS IN URINE

RELATED APPLICATIONS

This application is a continuation of U.S. application Ser No. 11/137,935, filed May 25, 2005, which claims priority to Italian patent application RM2005A000067, filed Feb. 17, 2005, each of which is incorporated herein by reference in its entirety.

INCORPORATION-BY-REFERENCE OF SEQUENCE LISTING

The contents of the text file named "29480-502C01US_ST25.txt", which was created on Oct. 14, 2011 and is 2.56 KB in size, are hereby incorporated by reference in their entirety.

FIELD OF THE INVENTION

The technical field of the invention is that of the molecular diagnosis of viral infections.

BACKGROUND OF THE INVENTION

Early analysis and the possibility of directly genotyping the pathogenic agent are among the principal objectives of research in the diagnostic field. The development of new diagnostic assays should also take into account a degree of compatibility to high-throughput screening methods and a high level of sensitivity for diagnoses made as soon as possible after the occurrence of the infection. In developing countries it is also important to take into account the ease of handling of biological samples, for more widespread distribution of the diagnostic assays.

There are currently three types of in vitro diagnostic systems: direct culture of the pathogenic agent from the biological sample, which is the so-called "gold standard" of diagnostic assays; immunological assays based on the detection of products or antigens of the infectious agent; and indirect immunological assays that can detect antibodies produced against the infectious agent during or after infection.

In the first system, the principal disadvantage is that the biological sample must be considered to be at risk, inasmuch as it can potentially transmit the pathogenic agent, whereas in the indirect detection of the antibodies there is no possibility of discriminating between past and current infections.

Molecular diagnostic methods have been developed that are based on the detection of the nucleic acids of the pathogenic agent in the blood or plasma samples, or in the cell cultures, taken from the patient. These tests are usually much more sensitive than the immunoassays. For this reason, and because of their specificity, they are extremely promising, but usually require special equipment and qualified personnel.

Molecular diagnostic methods based on transrenal DNA (TrDNA) have been described and their utility for monitoring the fate of allogeneic transplants, to detect the sex of a fetus, and to screen the presence of tumor markers was demonstrated. In particular, U.S. Pat. No. 6,251,638 describes an analytical method for detecting male fetal DNA in the urine of pregnant women; in U.S. Pat. No. 6,287,820, the invention is aimed at the diagnosis of tumors, particularly of adenocarcinomas (of the colon and pancreas); and in U.S. Pat. No. 6,492,144, the transrenal nucleic-acid analysis method is used to monitor the progress of allogeneic transplants, using known methods for molecular analysis. The presence of identifiable transrenal DNA in urine, in the fraction of DNA fragments consisting of 150 base pairs or more, was shown (Al-Yatama et al. (2001), "Detection of Y-chromosome-specific DNA in the plasma and urine of pregnant women using nested polymerase chain reaction"; Prenat Diagn, 21:399-402; and Utting, M., et al. (2002), "Microsatellite analysis of free tumor DNA in urine, serum, and plasma of patients: A minimally invasive method for the detection of bladder cancer"; Clin Cancer Res, 8:35-40).

Molecular detection of TrDNA in urine is performed using techniques that are very well known in the art and widely used in laboratory practice, such as PCR (polymerase chain reaction), hybridization, or the so-called "cycling probe reaction."

The presence of transrenal DNA has been explained as being the result of phenomenon of apoptosis. In the process of apoptosis or programmed cell death the nuclear DNA is cleaved into nucleosomes and oligomers, which subsequently, as a part of apoptotic process, are phagocytozed and removed from the organism. (Umansky, S. R., et al. (1982), "In vivo DNA degradation in thymocytes of gamma-irradiated or hydrocortisone-treated rats"; Biochim. Biophys. Acta, 655:9-17). A portion of this degraded DNA, though, escapes the phagocytosis, and appears in the bloodstream (Lichtenstein, A. V., et al. (2001), "Circulating nucleic acids and apoptosis"; Ann NY Acad Sci, 945:239-249), and, as confirmed in the above-referred patents, also in urine.

The presence of viral DNA that originates from sources outside of the urinary tract, in urine has not been described until now. Meanwhile, circulation of viral DNA released from the genome of transfected cell in the plasma has been shown: for example, fragments of Epstein-Barr viral DNA were detected in plasma of patients with nasopharyngeal carcinoma (Chan, K. C., et al. (2002), "Molecular characterization of circulating EBV DNA in the plasma of nasopharyngeal carcinoma and lymphoma patients"; Cancer Res 63:2028-2032), and in the case of human papilloma virus (HPV) in the plasma of patients with cervical cancer (Pornthanakasem, W., et al. (2001), "Human Papillomavirus DNA in plasma of patients with cervical cancer"; BMC Cancer 1:2).

SUMMARY OF THE INVENTION

The present invention relates to methods for diagnosis and monitoring of viral infections by detecting and quantifying transrenal viral NA-specific sequences. In embodiments, the nucleic acids are isolated or purified. The method also includes the fractionation of the urine sample, for example, through centrifugation or filtration, with the separation of a cell-free fraction from a fraction associated with the cell bodies.

Furthermore, in another embodiment, the sample is pretreated with a denaturing agent.

The analysis of the nucleic acids is performed using one of the following techniques: hybridization of the nucleic acids, the cycling probe reaction, a polymerase chain reaction, a nested polymerase chain reaction, single-strand conformation polymorphism, a ligase chain reaction, strand displacement amplification, and restriction fragment length polymorphism.

The method is applicable to all viral pathogenic agents, including RNA, DNA, episomal, and integrative viruses. It also applies to recombinant viruses, such as the adenoviruses or lentiviruses utilized in gene therapy. In particular, the methods apply to the following viruses: retroviruses, including recombinant and natural HIV-1, HIV-2, variola virus, poliovirus, herpes simplex virus (HSV), Epstein-Barr virus (EBV), hepatitis C virus (HCV), hepatitis B virus (HBV) and adenoviruses (AAV). In some embodiments the viral agents are Epstein-Barr virus (EBV) and HIV-1.

In another of its embodiments, the invention relates to a kit for the detection of viral nucleic acid in urine, including: reagents and/or materials for the fractionation and/or extraction of transrenal nucleic acids from urine, DNA probe, or pairs of specific oligonucleotides (primers) for at least one viral agent.

Unless otherwise defined, all technical and scientific terms used herein have the same meaning as commonly understood by one of ordinary skill in the art to which this invention relates. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

Other features and advantages of the invention will be apparent from the following detailed description and from the claims.

DETAILED DESCRIPTION OF THE INVENTION

The present definitions are offered for the purposes of the present invention:

Amplicon: A term for any relatively small, DNA fragment that is replicated, e.g., by PCR.

Amplification: An increase in the number of copies of a specific DNA fragment can occur in vivo or in vitro.

Apoptosis: Programmed cell death in normally functioning human and animal cells when age or state of cell health and condition dictate. An active process requiring metabolic activity by the dying cell, characterized by cleavage of the DNA into fragments that give a so called laddering pattern of DNA fragments of nucleosomal size and its oligomers.

Chaotropic: The property of chemical substances (e.g., ions such as $SCN^-$, $ClO_4^-$, and guanidine) that disturb the thermodynamic structure of water. It allows less polar and more hydrophobic substances to become more soluble in water. The effect at the biological level is the denaturation of proteins.

Episome: A circular DNA molecule of that can replicate independently of the cellular chromosome or integrate and replicate as part of the chromosome.

Gene: DNA fragment that contains sequences necessary to code for an mRNA, and to control the expression of these sequences.

Genome: The total set of genes of an organism enclosed, among the eukaryotes, in chromosomal structures.

Cyclic Probe Reaction: CPT reactions are performed at a constant specific temperature, which allows hybridization of the chimeric probe with its complementary single-stranded target DNA. Within the resulting target-probe duplex, RNase H recognizes the DNA-RNA hybrid and specifically cleaves the RNA portion of the probe. The cleaved fragments are not stable at the reaction temperature and disassociate from the target. The target is then free to hybridize with another probe molecule, and the cycle is repeated. The probe fragments accumulate, serving as a basis for the detection of target. Over time, the accumulation of cleaved probe fragments follows linear kinetics and therefore the amount of target can be quantified.

Hybridization: A widely used technique that exploits the ability of complementary sequences in single-stranded DNAs or RNAs to pair with each other to form a double helix. Hybridization can take place between two complimentary DNA sequences, between a single-stranded DNA and a complementary RNA, or between two RNA sequences. The technique is used to detect and isolate specific sequences, measure homology, or define other characteristics of one or both strands.

Infection: Invasion and multiplication of microorganisms in body tissues, which may be clinically unapparent or result in local cellular injury due to competitive metabolism, toxins, intracellular replication or antigen antibody response.

Ligase Chain Reaction: A method of DNA amplification similar to PCR. LCR differs from PCR because it amplifies the probe molecule rather than producing amplicon through polymerization of nucleotides. Two probes are used per each DNA strand and are ligated together to form a single probe. LCR uses both a DNA polymerase enzyme and a DNA ligase enzyme to drive the reaction Like PCR, LCR requires a thermal cycler to drive the reaction and each cycle results in a doubling of the target nucleic acid molecule. LCR can have greater specificity than PCR.

Nested PCR: A second PCR that is performed on the product of an earlier PCR using primer, which are internal to the originals. This significantly improves the sensitivity and specificity of the PCR.

Nested primer: A selected primer internal to an amplicon obtained with a first PCR cycle. The amplification process that uses at least one nested primer improves specificity, because the non-specific products of the first cycle are not amplified in the second cycle.

Nucleic Acid: Linear polymers of nucleotides, linked by 3',5' phosphodiester linkages. In DNA, deoxyribonucleic acid, the sugar group is deoxyribose and the bases of the nucleotides adenine, guanine, thymine and cytosine. RNA, ribonucleic acid, has ribose as the sugar and uracil replaces thymine. DNA functions as a stable repository of genetic information in the form of base sequence. RNA has a similar function in some viruses but more usually serves as an informational intermediate (mRNA), a transporter of amino acids (tRNA), in a structural capacity or, in some newly discovered instances, as an enzyme.

Oligonucleotide/Polynucleotide: Linear sequence of two or more nucleotides joined by phosphodiester bonds. Above a length of about 20 nucleotides the term "polynucleotide" is generally used.

Pathogenic agent: A pathogen is a biological agent that can cause disease to its host. A synonym of pathogen is "infectious agent". The term "pathogen" is most often used for agents that disrupt the normal physiology of a multicellular organism.

Pellet: Sediment, when cells are present, usually includes the cell fraction, or that can be obtained by centrifuging a biological sample.

Polymerase: Enzyme utilized in the amplification of nucleic acids. The term includes all of the variants of DNA polymerases.

Primer: Short pre-existing polynucleotide chain to which new deoxyribonucleotides can be added by DNA polymerase.

PCR: Polymerase Chain Reaction involving two synthetic oligonucleotide primers, which are complementary to two regions of the target DNA (one for each strand) to be amplified, are added to the target DNA (that need not be pure), in the presence of excess deoxynucleotides and Taq polymerase, a heat stable DNA polymerase. In a series (typically 30) of temperature cycles, the target DNA is repeatedly denatured (around 90° C.), annealed to the primers (typically at 50-60° C.) and a daughter strand extended from the primers (72° C.). As the daughter strands themselves act as templates for subsequent cycles, DNA fragments matching both primers are amplified exponentially, rather than linearly.

Probe: General term for a fragment of DNA or RNA corresponding to a gene or sequence of interest, that has been labelled either radioactively or with some other detectable molecule, such as biotin, digoxygenin or fluorescein.

Purification/Decontamination/Sterilization: Refers to a process for removing contaminants from a sample, where the result is a sample containing 60%, preferably 75%, and even more preferably 90% of the material toward which the purification procedure is directed.

Restriction Fragment Length Polymorphism (RFLP): A method that allows genetic relationship established by comparing the characteristic polymorphic patterns that are obtained when certain regions of genomic DNA are amplified (typically by PCR) and cut with certain restriction enzymes. Variations in such patterns are generated by mutations that create or abolish recognition sites for these enzymes Sample: The term is broadly interpreted and includes any form that contains nucleic acids (DNA or RNA) in solution or attached to a solid substrate, where the definition of "nucleic acids" includes genomic DNA (for example, when it is attached to a solid substrate, such as in the Southern Blot or in solution), cDNA, and other forms.

Combinations of two nucleic-acid sequences through hybridization are formed thanks to the hydrogen bonds between G and C or A and T bases or analogs of these bases. These combinations are complementary, and the DNA helixes are anti-parallel. This hybridization combination can be created with one sequence (or helix) in a solution and the other attached to a solid phase (such as, for example, in the FISH [fluorescent in situ hybridization] method), or else with both of the sequences in solution.

Single-Strand Conformation Polymorphism (SSCP): SSCP is the electrophoretic separation of single-stranded nucleic acids based on subtle differences in sequence (often a single base pair) that results in a different secondary structure and a measurable difference in mobility through a gel.

Strand Displacement Amplification (STA): STA is an isothermal, in vitro nucleic acid amplification technique based upon the ability of HincII to nick the unmodified strand of a hemiphosphorothioate form of its recognition site, and the ability of exonuclease deficient Klenow fragment of DNA Polymerase (exo-klenow) to extend the 3'-end at the nick and displace the downstream DNA strand. Exponential amplification results from coupling sense and antisense reactions in which strands displaced from a sense reaction serve as target for an antisense reaction and vice versa.

Target sequence: Nucleic-acid sequence that should be analyzed through hybridization, amplification, or other methods or combinations of methods.

Tm (melting temperature): Temperature at which a specific double-helix DNA population dissociates into single-strand polymers. The formula for calculating this temperature for polynucleotide fragments is well known in the art: Tm=81.5+0.41 (% G+C) (Anderson & Young, "Quantitative Filter Hybridization," in *Nucleic Acid Hybridization* [1985]). For oligonucleotides with fewer than 40 base pairs, a simplified formula can be used: Tm=3° C.×(G+C)+2×(A+T).

Tr-DNA/RNA: Transrenal DNA/RNA, or DNA/RNA present in urine after having been passed through the kidney barrier.

Urinary tract: Includes the organs and ducts that participate in the elimination of urine from the body.

Transrenal Nucleic Acids (TrNAs) in Viral Infection

The present invention is based on the discovery that following a viral infection, the nucleic acids of the virus (es) or of viral origin are cleaved to a relatively short fragments which cross the transrenal barrier (these nucleic acids are generally termed TrNA, or TrDNA or TrRNA) and can be detected in urine as cell-free low-molecular-weight fragments (whose length is less than 1000 nucleotides) through molecular methods. As used herein, the term "viral nucleic acid" encompasses nucleic acids of viral origin.

The presence of transrenal nucleic acids (Tr-NA) in urine was detected previously only in hosts who had undergone heterologous tissue or organ transplants, in the case of women pregnant with male fetuses, and in the case of tumors characterized by specific marker genes. The presence of transrenal nucleic acids of viral origin in the case of viral infections according to the present invention is also, and preferably, detected in the case of non-urinary-tract infections, even in the absence of hematuria or of pathologies that lead to the rupture, or that alter the normal integrity, of the renal barrier.

Transrenal nucleic acids (Tr-NA) of viral origin are not associated with, and are not derived from, the genome of cells that are lost or released in the urinary tract and that are found in urine. Instead, the nucleic acids according to the present invention are filtered by the glomerular-renal filtration mechanism. Thus, the dimensions of the transrenal nucleic-acid fragments are generally smaller than about 1000 base pairs, e.g., smaller than about 500, smaller than about 300, smaller than about 250, or between about 100 and about 200 base pairs, as opposed to other situations in which DNA usually has a high molecular weight and a length in excess of 1000 bases or base pairs.

Therefore, in the present invention, the transrenal nucleic acid (TrNA) of viral origin is generally not found in the urine sediment, but in the soluble fraction, although traces of TrNA can co-sediment with the cells during centrifuging.

Thus, the discovery makes it possible, for the first time, to confirm the presence of transrenal viral NA directly in urine, and thus is applicable to the diagnosis and monitoring of any infectious disease that has a viral etiology.

Therefore, in embodiments, the invention relates to methods for diagnosis or monitoring of viral infection by determining the presence of viral nucleic acids, preferably viral DNA or NA of viral origin, in a urine sample. The methods includes the step of determining the presence of transrenal viral NA using methods generally used in laboratory practice such as hybridization, PCR, nested PCR, SSCP, LCR, and SDA.

In certain embodiments, the methods according to the invention include an initial treatment of the urine sample prior to the determination of the presence of transrenal viral nucleic acids. In an embodiment, the invention includes the pretreatment of the urine sample with an agent that inhibits the degradation of the DNA or RNA. These agents include the enzymatic inhibitors, such as chelating agents, detergents, or denaturing agents, DNase or RNase inhibitors, which are preferably selected from the group consisting of EDTA, guanidine HCl, guanidine isothiocyanate, N-lauryl sarcosine, and sodium dodecyl sulfate.

In another embodiment, the determination of the presence of transrenal viral nucleic acids optionally be preceded by centrifugation or filtration of the urine sample in order to separate the cellular fraction of the urine from the cell-free low-molecular-weight nucleic acids (DNA/RNA). However, the urine sample may also be utilized without fractionation. Centrifugation is preferably performed at a speed between 2500 g and 4500 g, and more preferably between 3000 g and 4000 g. Filtration is preferred to carry out through a filter with pore size between 0.1 and 5.0 µm, more preferably with pore size between 0.2 and 1.0 µm and even more preferably 0.45 and 0.8 µm. Equivalent methods for separating the soluble fraction from the cellular fraction may also be used.

Yet in another further embodiment, step b) may optionally be preceded by isolation and/or purification of transrenal nucleic acids. In its turn isolation/purification step may be optionally preceded by filtration or centrifugation or equivalent technique of urine fractionation.

The isolation and/or purification of the transrenal nucleic acids is achieved through the use of chemical or physical methods that are already known in the art. It includes one or more purification steps using methods selected from among extraction with organic solvents, filtration, precipitation, absorption on solid matrices (e.g., silica resin, hydroxyapatite or ion exchange), affinity chromatography (e.g., via sequence specific capture or nucleic acid specific ligands), or else molecular exclusion chromatography. However, the purification method must be appropriate for the isolation of DNA (single- or double-strand) whose dimensions are smaller than 1000 nucleotide pairs. Even more preferably, the purification is specific for fragments that are smaller than 500 nucleotides, and even more preferably, fragments whose length are less than 300 or 250 base pairs, or that are between 100 and 200 bases or base pairs. The purification preferably takes place on a matrix consisting but not limited to a silica resin.

In one preferred embodiment, the DNA isolation method is implemented by pretreating the urine sample with a denaturing agent, as described above, e.g., urea, guanidine HCl, or guanidine isothiocyanate, at room temperature. Guanidine isothiocyanate is preferably utilized. The sample is then passed through a solid phase, preferably a matrix consisting of a silica resin that, in the presence of chaotropic salts (guanidine isothiocyanate), binds the nucleic acids. The sample is then collected or eluted in a buffer, such as Tris-EDTA (Tris 10 mM, EDTA 1 mM), or in water.

In another preferred embodiment, the characterization and the determination of the presence of transrenal viral NA in step b) are performed through a technique selected from the group consisting of: hybridization of the nucleic acids, a cycling probe reaction (F. Bekkaoui et al., in *BioTechniques* 20:240-248 [1996]), a polymerase chain reaction (*PCR Protocols: A Guide to Methods and Applications*, by M. Innis et al.; Elsevier Publications, 1990), a nested polymerase chain reaction, single-strand conformation polymorphism, a ligase chain reaction (LCR) (F. Barany, in *PNAS USA,* 88:189-93 [1991]), strand displacement amplification (SDA) (G. K. Terrance Walker, et al., in *Nucleic Acid Res,* 22:2670-77 [1994], and restriction fragments length polymorphism (RFLP). A technician in the field might also use combinations of these methods, e.g., PCR-Restriction Length Polymorphism, in which the nucleic acids are amplified, and then divided into aliquots and digested with restriction enzymes, and then separated via electrophoresis.

Polymerase chain reaction (PCR) is the preferred method for the detection and/or quantitative analysis of nucleic acids. Yet more preferred is the nested PCR method, as defined above, or the semi-nested PCR method, in which only one of the two primers is internal to the amplicon.

The advantage of the method is linked primarily to the ease of collecting the biological samples; to the fact that the transrenal nucleic acids are not infectious; and to the sensitivity of the molecular diagnostic method that can be applied to the nucleic acids, even in the form of fragments.

The diagnostic method is applicable to all viral pathogenic agents, including RNA, DNA, episomal, or integrated viruses. It also applies to recombinant viruses, such as the adenoviruses or lentiviruses utilized in gene therapy. In particular, the method preferably applies to the following viruses: recombinant and natural HIV-1, HIV-2, variola virus, poliovirus, herpes simplex virus (HSV), Epstein-Barr virus (EBV), hepatitis C virus (HCV), hepatitis B virus (HBV) and adenoviruses (AAV).

The method is preferably applied to the HIV-1 virus, with the selection of probes or primer oligonucleotides in the GAG, POL, or TAT region for the detection. Particularly preferred pairs of primers are the ones consisting of the specific sequences for the HIV GAG region, and preferably the ones corresponding to the IDN 1-4 sequence, and the ones that are specific for the HIV-1 POL region, preferably the ones corresponding to the IDN 5-7 region, when the detection is performed via a polymerase chain reaction (PCR), and, in particular, via nested (GAG) or semi-nested (POL) PCR.

In another of its embodiments, the invention relates to a kit for the detection and monitoring of transrenal viral NA in urine, including: reagents and/or materials for the separation and/or purification of transrenal DNA from a urine sample, DNA probes, or pairs of specific oligonucleotides (primers) for at least one viral agent. Reaction tubes, agents for the pretreatment of the sample, enzymes for labeling the probe, and enzymes for the amplification of the DNA may optionally be present.

In a preferred embodiment, the kit includes pairs of oligonucleotide primers that are specific for recombinant and natural HIV-1, HIV-2, variola virus, poliovirus, herpes simplex virus (HSV), Epstein-Barr virus (EBV), hepatitis C virus (HCV), hepatitis B virus (HBV), adenoviruses (AAV); or, yet more preferably, primers that are selected from the group consisting of the sequences listed below, and specific reagents for the polymerization chain reaction, preferably in nested or semi-nested form.

EXAMPLES

The technician in the field may modify all of the methodology described herein with no change in the basic principal idea.

Example 1

Preparation of the Urine Samples

The method for the preparation of the urine samples and for the extraction of the DNA is described in PCT patent No. WO 98/54364, which is incorporated by reference in its entirety. All of the steps of the preparation of the urine samples and of the analysis of the transrenal DNA were performed at room temperature. Briefly, approximately 50-60 ml of urine samples were collected from each patient participating in the study. Within 30 minutes after collection, a solution consisting of 0.5M EDTA and 0.5M Tris-HCl, at a pH of 8.5 and at a final concentration of 10 mM, was added in order to inhibit the nucleases that might be present in urine samples. The EDTA has the effect of inhibiting the nucleases associated with divalent ions, while the high pH inhibits the acid nucleases.

The stabilized urine samples can be stored, in aliquots of 5 ml, at −80° C. In some instances, the samples were centrifuged for 15 minutes at 3500 g, and in this case the extraction and the analysis of the DNA were performed on both the supernatant and the sediment.

Example 2

Extraction of the DNA from the Urine Samples

In this study, no commercial kits were used to extract the DNA. In fact, most of the commercial kits utilized for DNA purification are designed to isolate high-molecular-weight DNA, starting from various types of biological material.

Bearing in mind that transrenal DNA has a relatively low molecular weight (approximately 150-200 bp), fragments of this size can be isolated from the soluble portion of the urine, even if, in a majority of cases, the DNA is isolated from non-fractionated urine samples, because a portion of the Tr-DNA could be lost, due to the tendency of the Tr-DNA to co-sediment with cells and particulate material during the centrifugation of the urine sample.

The transrenal DNA was isolated by adding two volumes of 6 M guanidine isothiocyanate to 5 ml of whole urine, or to an equal volume of the fractions previously obtained through centrifugation. The resulting solution was mixed vigorously.

The soluble low-molecular-weight DNA was captured by Wizard resin (Wizard Resin Suspension, Promega), transferred to a mini-column and washed thoroughly (through repeated use of large volumes of the washing buffer supplied with the resin). The Tr-DNA was eluted with water or with 10 mM Tris-HCl at a pH of 7.5-1 mM EDTA.

Example 3

Design of PCR Primers

The primers for analysis of Tr-DNA based on the use of PCR were selected for two different sizes of the target fragment, i.e., one in the range from 60 to 120 by and the other in the range from 250 to 400 bp. All of the primers were also compared against the complete human genome sequence. The primers were designed using the FastPCR software package (biocenter.helsinkifi/bi/bare-1_html/oligos). The primers for the nested-PCR analysis were selected using the Primer 3 package, which is available at the frodo.wi.mit.edu/cg-i-bin/primer3/primer3_www.cgi site, in such a way that the melting temperature of the internal, nested primers was not lower than that of the external primers.

The HIV primers were selected for recognition of all 9 of the Type M HIV subtypes. In accordance with the recently revised nomenclature (i.e., the 1999 Nomenclature Proposal: [hivlan1.gov/content/hiv-db/HTML/reviews/nomenclature/Nomen]), the HIV-1 M group subtypes are represented by phylogenetically associated groups of HIV-1 sequences. They are designated as A1, A2, B, C, D, F1, F2, G, H, J, and K. The M group contains viruses that represent approximately 95% of all of the cases of HIV in Europe. Complete genomic sequences of HIV-1 M group subtypes were obtained from the database at the Los Alamos National Laboratory (New Mexico, hiv.lanl.gov). The multiple alignments and the creation of consensus sequences of the various subtypes were performed through the use of ClustalX algorithm included in the BioEdit package (mbio.ncsu.edu/BioEdit/bioedit.html).

The following primers were selected:
GAG Primers for Nested PCR.

```
External:
GAG 468-F (SEQ ID NO: 1):
TGGGTAAAAGTAATAGAGGAGAAGGC;

GAG 602-R (SEQ ID NO: 2):
AACATTTGCATGGCTGCTT.

Product: 134 bp.

Internal:
GAG 518-F (SEQ ID NO: 3):
CAGCATTATCAGAAGGAGCCACC;

GAG 596-R (SEQ ID NO: 4):
TGCATGGCTGCTTGATGTCC.

Product: 79 bp.
```

POL Primers for Semi-Nested-PCR, Short Amplicon

```
External primers:
POL 4368-F (SEQ ID NO: 5):
GGRGAAGCCWTGCATGGAC;

POL 4468-R (SEQ ID NO: 6):
GCTACATGRACTGCTACCAG.

Product: 102 bp.

Internal primers:
POL 4368-F (SEQ ID NO: 5):
GGRGAAGCCWTGCATGGAC;

POL 4427-Rn (SEQ ID NO: 7):
TGTRCAATCTARTTGCCATATYCCTGG.

Product: 60 bp.
```

POL Primers for Semi-Nested-PCR, Long Amplicon

```
External primers:
POL 4368-F (SEQ ID NO: 5):
```

```
-continued
GGRGAAGCCWTGCATGGAC

POL 4678-R (SEQ ID NO: 8):
ACTCCYTGRCTTTGGGGATTG

Product: 311 bp.

Internal primers (nested):
POL 4368-F (SEQ ID NO: 5):
GGRGAAGCCWTGCATGGAC

POL 4427-Rn (SEQ ID NO: 7):
TGTRCAATCTARTTGCCATATYCCTGG.

Product: 60 bp.
```

TAT Primers for Semi-Nested PCR (Long Amplicon)

```
External primers:
TAT 5955-F (SEQ ID NO: 9):
GCTTAGGCATYTCCTATGGCAG

TAT 6462-R (SEQ ID NO: 10):
TGGGGTCTGTKGGTACACAGG.

Product: 569 bp.

Internal primers:
TAT 6330-Fn (SEQ ID NO: 11):
CWGTHTAYTATGGRGTACCTGTGTGG

TAT 6462-R (SEQ ID NO: 10):
TGGGGTCTGTKGGTACACAGG.

Product: 132 bp.
```

Example 4

Diagnosis of HIV-1 Infection Based on TrDNA

The DNA was isolated from the urine samples of 10 patients infected with HIV, as described in the preceding examples. These patients were clinically diagnosed as being infected with HIV through the use of standard clinical molecular tests to detect the presence of antibodies that are specific for the HIV virus.

Figure 1:
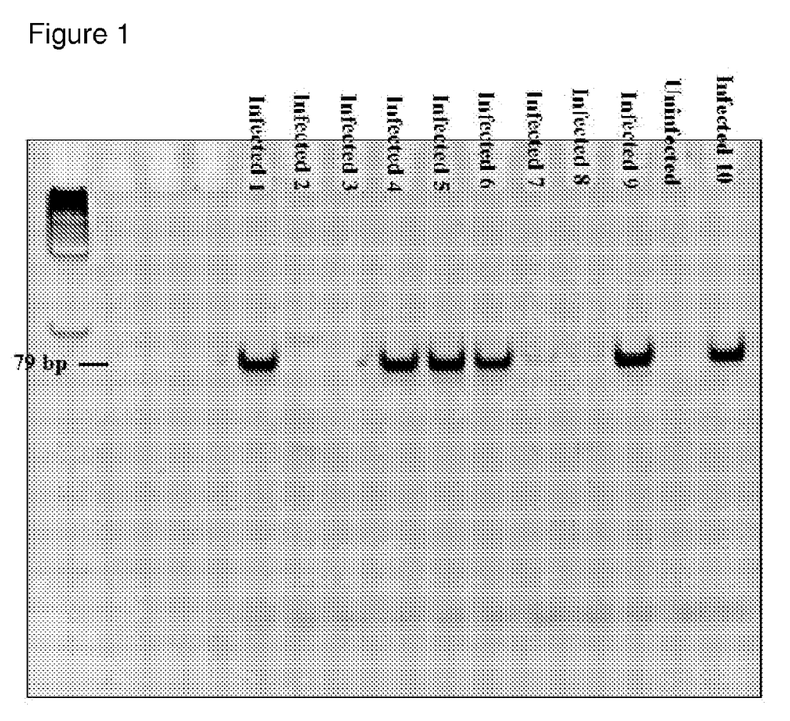
FIG. 1 is a photographic image showing the results of gel electrophoresis of the amplification product obtained through nested PCR of the transrenal DNA of non-fractionated urine samples of patients infected with HIV-1 (20 cycles with the 468/602 primer pair [134 bp] followed by 35 cycles with 518/596 [79 bp]). The primers are specific for the HIV-1 GAG region.
Figure 2:
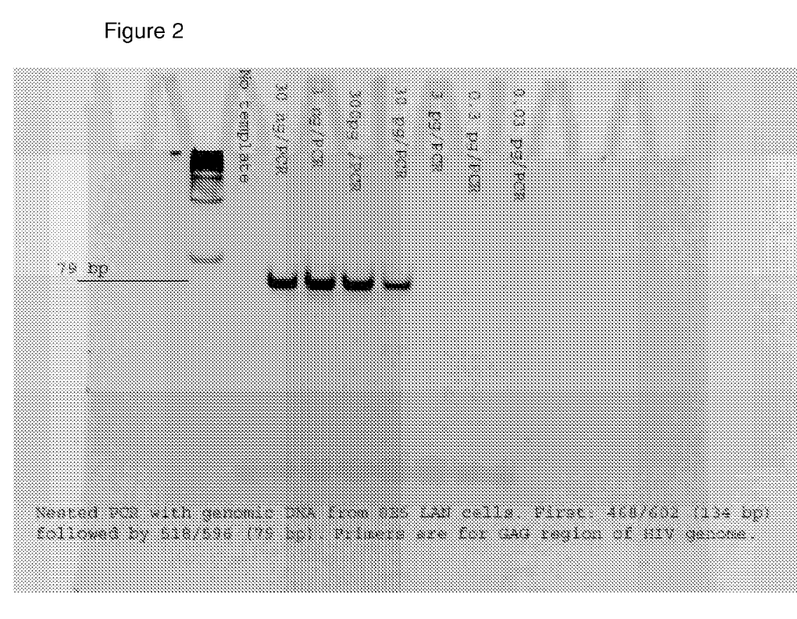
FIG. 2 is a photographic image showing the results of gel electrophoresis of the amplification product obtained through nested PCR of the genomic DNA extracted from 8E5 LAV cells (20 cycles with the 468/602 primer pair [134 bp] followed by 35 cycles with 518/596 [79 bp]). The primers are specific for the HIV-1 GAG region.
Figure 3:
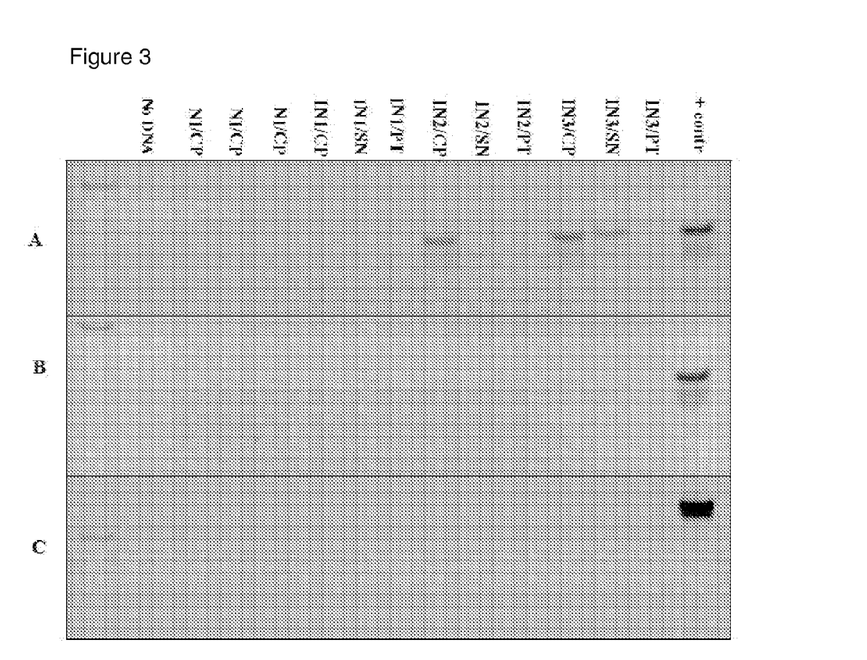
FIG. 3 is a photographic image showing the results of gel electrophoresis of the amplification product obtained through nested PCR of the transrenal DNA of urine samples of patients infected with HIV-1 (CP: complete; SN: supernatant; PT: pellet). A-102 bp/60 bp (specific primers for the HIV-1 POL region); B-317 bp/60 bp (specific for POL); C-569 bp/132 bp (specific for TAT); NI: non-infected; IN 1-3: patients infected with HIV.

FIG. 1 shows the electrophoresis of the HIV-1 DNA fragments, as amplified via nested PCR, with the above-indicated two pairs of GAG-specific primers, in accordance with the method described in the invention. A band whose dimensions correspond to the ones that were expected as the result of the nested PCR amplification—as performed with the use of the 468/602 pair of primers in the first amplification, followed by the 518/596 pair (79 bp)—was observed in the urine of 8 of the 10 patients and in the positive controls, but not in the negative controls.

Table 1 indicates the viral load of each of the patients who were analyzed, from which it can be inferred that in the case of the samples (numbers 2 and 3) that were negative upon amplification, the viral load was lower than 50 copies of the virus per ml of plasma.

TABLE 1

Viral load of the HIV-infected patients.

| Patient No. | Infection | HIV load |
|---|---|---|
| 1 | HIV | 120,000 |
| 2 | HIV | <50 |
| 3 | HIV | <50 |
| 4 | HIV | 867 |
| 5 | HIV | 88,000 |
| 6 | HIV | 8,370 |
| 7 | HIV | 32,046 |
| 8 | HIV + HCV | 500,000 |
| 9 | HIV | 15,822 |
| 10 | HIV + HCV | <50 |

The viral load was determined by measuring the quantity of the HIV-specific RNA via RT-PCR in the plasma.

The apparent sensitivity of the nested PCR was evaluated by amplifying, with the same pair of primers, an 8E5 LAV cell line genomic DNA carrying a single integrated copy of the HIV genome. The sensitivity was determined to be 5 genome equivalents.

Sequence list

```
GAG 468-F (seq. No. 1):
TGGGTAAAAGTAATAGAGGAGAAGGC;

GAG 602-R (seq. No. 2):
AACATTTGCATGGCTGCTT;

GAG 518-F (seq. No. 3):
CAGCATTATCAGAAGGAGCCACC;

GAG 596-R (seq. No. 4):
TGCATGGCTGCTTGATGTCC.

POL 4368-F (seq. No. 5):
GGR*GAAGCCW*TGCATGGAC;

POL 4468-R (seq. No. 6):
GCTACATGR*ACTGCTACCAG;

POL 4427-Rn (seq. No. 7):
TGTRCAATCTARTTGCCATATY*CCTGG

POL 4678-R (seq. No. 8):
ACTCCY*TGR*CTTTGGGGATTG

TAT 5955-F (seq. No. 9):
GCTTAGGCATY*TCCTATGGCAG

TAT 6462-R (seq. No. 10):
TGGGGTCTGTK*GGTACACAGG

TAT 6330-Fn (seq. No. 11):
CW*GTHTAY*TATGGRGTACCTGTGTGG

Nucleotides indicated by an asterisk (*) indicate
degenerate nucleotides known to those skilled in
the art.
```

Equivalents

Although particular embodiments have been disclosed herein in detail, this has been done by way of example for purposes of illustration only, and is not intended to be limiting with respect to the precise form of the disclosed invention or to the scope of the appended claims that follow. In particular, it is contemplated by the inventors that various substitutions, alterations, and modifications may be made to the invention without departing from the spirit and scope of the invention as defined by the claims. Various alterations and modifications of the invention are believed to be a matter of routine for a person of ordinary skill in the art with knowledge of the embodiments described herein. Other aspects, advantages, and modifications considered to be within the scope of the following claims.

The invention claimed is:

1. A method for diagnosing a virus infection in a subject, comprising
   a) obtaining a urine sample from a subject;
   b) separating a soluble fraction of said urine sample; and
   c) detecting the presence of a cell-free virus nucleic acid in said soluble fraction of said urine sample, wherein said nucleic acid is less than about 300 bp in length, wherein said detecting is performed by a method selected from the group consisting of PCR, nested PCR, SSCP, LCR, and SDA, using a primer set comprising
   at least one forward primer selected from the group consisting of SEQ ID NOs: 1 and 3 and at least one reverse primer selected from the group consisting of SEQ ID NOs: 2 and 4, or
   a forward primer of SEQ ID NO: 5 and at least one reverse primer selected from the group consisting of SEQ ID NOs: 6 and 7, or
   a forward primer of SEQ ID NO: 11 and a reverse primer of SEQ ID NO: 10,
   wherein the presence of said nucleic acid diagnoses a viral infection.

2. The method of claim 1, further comprising the step of quantifying the nucleic acid.

3. The method of claim 1, wherein the subject is a mammal.

4. The method of claim 3, wherein the mammal is a human.

5. A method for diagnosing a virus infection in a subject, comprising
   a) obtaining a urine sample from a subject;
   b) separating a soluble fraction of said urine sample; and
   c) detecting the presence of a cell-free virus nucleic acid in said soluble fraction of said urine sample by a method selected from the group consisting of PCR, nested PCR, SSCP, LCR, and SDA, using a forward primer of SEQ ID NO: 5 and a reverse primer of SEQ ID NO: 8, wherein the presence of said nucleic acid diagnoses a viral infection.

6. The method of claim 5, further comprising the step of quantifying the nucleic acid.

7. The method of claim 5, wherein the subject is a mammal.

8. The method of claim 7, wherein the mammal is a human.

9. A method for diagnosing a virus infection in a subject, comprising
   a) obtaining a urine sample from a subject;
   b) separating a soluble fraction of said urine sample; and
   c) detecting the presence of a cell-free virus nucleic acid in said soluble fraction of said urine sample by a method selected from the group consisting of PCR, nested PCR, SSCP, LCR, and SDA, using a forward primer of SEQ ID NO: 9 and a reverse primer of SEQ ID NO: 10, wherein the presence of said nucleic acid diagnoses a viral infection.

10. The method of claim 9, further comprising the step of quantifying the nucleic acid.

11. The method of claim 9, wherein the subject is a mammal.

12. The method of claim 11, wherein the mammal is a human.

13. The method of claim 2, wherein said primer set comprises at least one forward primer selected from SEQ ID NOs: 1 and 3 and at least one reverse primer selected from SEQ ID NOs: 2 and 4.

14. The method of claim 4, wherein said primer set comprises at least one forward primer selected from SEQ ID NOs: 1 and 3 and at least one reverse primer selected from SEQ ID NOs: 2 and 4.

15. The method of claim 2, wherein said primer set comprises a forward primer of SEQ ID NO: 5 and at least one reverse primer selected from the group consisting of SEQ ID NOs: 6 and 7.

16. The method of claim 4, wherein said primer set comprises a forward primer of SEQ ID NO: 5 and at least one reverse primer selected from the group consisting of SEQ ID NOs: 6 and 7.

17. The method of claim 2, wherein said primer set comprises a forward primer of SEQ ID NO: 11 and a reverse primer of SEQ ID NO: 10.

18. The method of claim 4, wherein said primer set comprises a forward primer of SEQ ID NO: 11 and a reverse primer of SEQ ID NO: 10.

* * * * *

SEQUENCE LISTING

<160> NUMBER OF SEQ ID NOS: 11

<210> SEQ ID NO 1
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 1
tgggtaaaag taatagagga gaaggc                                    26

<210> SEQ ID NO 2
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 2
aacatttgca tggctgctt                                            19

<210> SEQ ID NO 3
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 3
cagcattatc agaaggagcc acc                                       23

<210> SEQ ID NO 4
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 4
tgcatggctg cttgatgtcc                                           20

<210> SEQ ID NO 5
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 5
ggrgaagccw tgcatggac                                            19

<210> SEQ ID NO 6
<211> LENGTH: 20
<212> TYPE: DNA
<213> ORGANISM: Artificial sequence
<220> FEATURE:
<223> OTHER INFORMATION: Oligonucleotide primer

<400> SEQUENCE: 6
gctacatgra ctgctaccag                                           20

<210> SEQ ID NO 7
<211> LENGTH: 27
<212> TYPE: DNA

```
<213> ORGANISM: Artificial sequence
<220> FEATURE:
<223> OTHER INFORMATION: Oligonucleotide primer

<400> SEQUENCE: 7
tgtrcaatct arttgccata tycctgg                                27

<210> SEQ ID NO 8
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 8
actccytgrc tttggggatt g                                      21

<210> SEQ ID NO 9
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 9
gcttaggcat ytcctatggc ag                                     22

<210> SEQ ID NO 10
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 10
tggggtctgt kggtacacag g                                      21

<210> SEQ ID NO 11
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 11
cwgthtayta tggrgtacct gtgtgg                                 26
```